US011164098B2

(12) United States Patent
Fokoue-Nkoutche et al.

(10) Patent No.: US 11,164,098 B2
(45) Date of Patent: Nov. 2, 2021

(54) AGGREGATING SIMILARITY METRICS

(71) Applicant: INTERNATIONAL BUSINESS MACHINES CORPORATION, Armonk, NY (US)

(72) Inventors: Achille B. Fokoue-Nkoutche, White Plains, NY (US); Arun K. Iyengar, Yorktown Heights, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 817 days.

(21) Appl. No.: 15/966,096

(22) Filed: Apr. 30, 2018

(65) Prior Publication Data

US 2019/0332964 A1   Oct. 31, 2019

(51) Int. Cl.
*G06N 7/02* (2006.01)
*G16B 40/00* (2019.01)

(52) U.S. Cl.
CPC ............... *G06N 7/02* (2013.01); *G16B 40/00* (2019.02)

(58) Field of Classification Search
None
See application file for complete search history.

(56) References Cited

U.S. PATENT DOCUMENTS

| | | | |
|---|---|---|---|
| 2004/0091933 A1* | 5/2004 | Stoughton | G01N 33/6803 435/7.1 |
| 2006/0173663 A1 | 8/2006 | Langheier et al. | |
| 2007/0027636 A1 | 2/2007 | Rabinowitz | |
| 2008/0133141 A1 | 6/2008 | Frost | |
| 2012/0041277 A1 | 2/2012 | Ebadollahi et al. | |
| 2015/0310163 A1 | 10/2015 | Kingsmore et al. | |
| 2016/0283679 A1 | 9/2016 | Hu et al. | |
| 2017/0242959 A1 | 8/2017 | Page et al. | |
| 2018/0322958 A1* | 11/2018 | Kalafatis | G06F 7/08 |
| 2019/0332947 A1 | 10/2019 | Fokoue-Nkoutche | |
| 2019/0333645 A1 | 10/2019 | Fokoue-Nkoutche | |
| 2020/0394241 A1* | 12/2020 | Kenedy | G06F 16/24578 |

OTHER PUBLICATIONS

Cheng et al., "DisSim: An Online System for Exploring Significant Similar Diseases and Exhibiting Potential Therapeutic Drugs," Scientific Reports, Jul. 26, 2016, p. 1-6.

(Continued)

*Primary Examiner* — Alan Chen
(74) *Attorney, Agent, or Firm* — Anthony R. Curro

(57) ABSTRACT

A method, computer system, and a computer program product for determining a composite similarity metric for data of a first data type is provided. The present invention may include providing a plurality of similarity metrics for the first data type. The present invention may also include providing a metric quantifying correlation of entities belonging to the first data type and entities belonging to a second data type. The present invention may then include developing a first regression model to predict values of the provided metric quantifying correlation of entities belonging to the first data type and entities belonging to the second data type using the provided plurality of similarity metrics. The present invention may further include calculating the composite similarity metric from a plurality of first regression coefficients in the developed first regression model.

22 Claims, 8 Drawing Sheets

(56) References Cited

OTHER PUBLICATIONS

Fokoue et al., "Predicting Drug-Drug Interactions Through Large-Scale Similarity-Based Link Prediction," ESWC 2016: The Semantic Web: Latest Advances and New Domains, 2016, p. 774-789, LNCS 9678, Springer International Publishing, Switzerland.
Hoehndorf et al., "Analysis of the Human Diseasome Using Phenotype Similarity Between Common, Genetic, and Infectious Diseases," Scientific Reports, Jun. 8, 2015, p. 1-14.
Mathur et al., "Finding Disease Similarity Based on Implicit Semantic Similarity," Journal of Biomedical Informatics, Apr. 2012, p. 363-371, vol. 45, Issue 2, Elsevier Inc.
Mell et al., "The NIST Definition of Cloud Computing," National Institute of Standards and Technology, Sep. 2011, p. 1-3, Special Publication 800-145.
Osborne et al., "Annotating the Human Genome with Disease Ontology," BMC Genomics, Jul. 7, 2009, 8 Pages, vol. 10, Supplement 1, BioMed Central.
Zhao et al., "An Object-Oriented Regression for Building Disease Predictive Models with Multi-Allelic HLA Genes," Genetic Epidemiology, May 2016, p. 1-30, vol. 40, Issue 4.
IBM, List of IBM Patents or Patent Applications Treated as Related, Appendix P, dated Apr. 7, 2021, 2 pages.

\* cited by examiner

AGGREGATING SIMILARITY METRICS

BACKGROUND

The present invention relates generally to the field of computing, and more particularly to biomedical informatics.

Similarity between diseases may be estimated by utilizing at least one quantitative metric (i.e., disease similarity metric). Disease similarity metrics may be based on a number of factors. These disease similarity metrics can be used for studying a variety of important problems including understanding and treating diseases, disease-gene associations, and finding appropriate drugs to treat diseases. If two diseases are similar based on a similarity score, then a treatment which works on one disease may also work on the second disease.

A variety of disease similarity metrics have been proposed. Semantic-based similarity considers the structure of a known disease taxonomy structure such as Disease Ontology.

Disease similarity may be based on phenotypes, which are observable characteristics of an organism arising from its response to the environment. Other methods may be used for disease similarity metrics (e.g., gene-based similarity, comorbidity-based similarity).

SUMMARY

Embodiments of the present invention disclose a method, computer system, and a computer program product for determining a composite similarity metric for data of a first data type. The present invention may include providing a plurality of similarity metrics for the first data type. The present invention may also include providing a metric quantifying correlation of entities belonging to the first data type and entities belonging to a second data type. The present invention may then include developing a first regression model to predict values of the provided metric quantifying correlation of entities belonging to the first data type and entities belonging to the second data type using the provided plurality of similarity metrics. The present invention may further include calculating the composite similarity metric from a plurality of first regression coefficients in the developed first regression model.

BRIEF DESCRIPTION OF THE SEVERAL VIEWS OF THE DRAWINGS

These and other objects, features and advantages of the present invention will become apparent from the following detailed description of illustrative embodiments thereof, which is to be read in connection with the accompanying drawings. The various features of the drawings are not to scale as the illustrations are for clarity in facilitating one skilled in the art in understanding the invention in conjunction with the detailed description. In the drawings.

DETAILED DESCRIPTION

Figure 1:
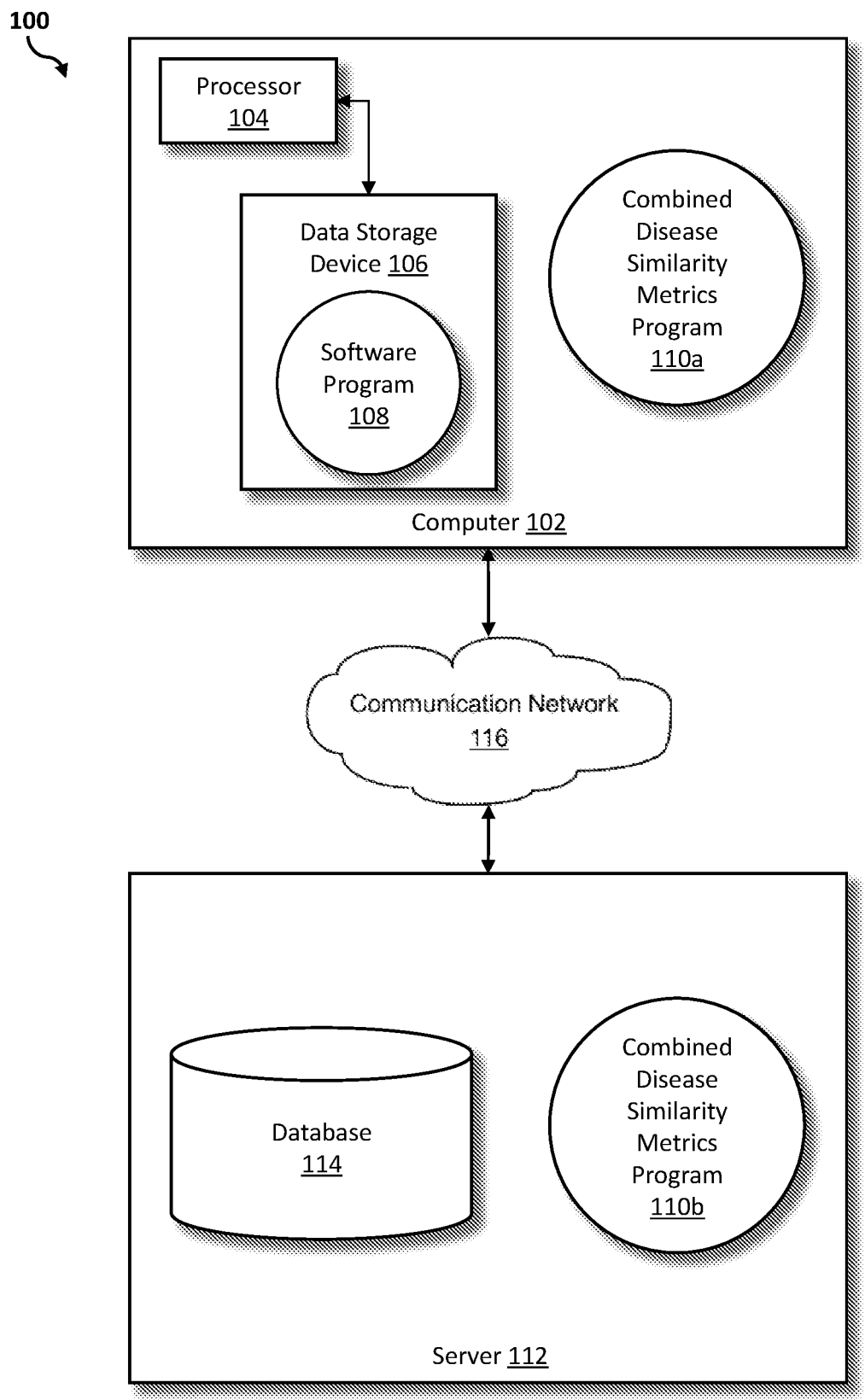
FIG. 1 illustrates a networked computer environment according to at least one embodiment.

Detailed embodiments of the claimed structures and methods are disclosed herein; however, it can be understood that the disclosed embodiments are merely illustrative of the claimed structures and methods that may be embodied in various forms. This invention may, however, be embodied in many different forms and should not be construed as limited to the exemplary embodiments set forth herein. Rather, these exemplary embodiments are provided so that this disclosure will be thorough and complete and will fully convey the scope of this invention to those skilled in the art. In the description, details of well-known features and techniques may be omitted to avoid unnecessarily obscuring the presented embodiments.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language, Python programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The following described exemplary embodiments provide a system, method and program product for determining a composite similarity metric for data of a first data type. As such, the present embodiment has the capacity to improve the technical field of biomedical informatics by incorporating multiple disease similarity metrics into bioinformatics calculations to identify potential treatments. More specifically, the combined disease similarity metrics program may utilize a ground truth data set related to diseases that represents correlations between diseases and genes, for example. Disease similarity metrics may be utilized to predict data in the ground truth data set, and a supervised learning method (e.g., a linear regression) may be utilized to determine an optimal method for combining disease similarity metrics. Other learning methods (e.g., random forest, gradient-boosted trees, neural networks) may also be utilized for combining disease similarity metrics. The optimized model that may include the combined disease similarity metrics may then be utilized to provide recommendations for treatments of similar diseases based on the disease similarity.

As previously described, similarity between diseases may be estimated by utilizing at least one quantitative metric (i.e., disease similarity metric). Disease similarity metrics may be based on a number of factors. These disease similarity metrics can be used for studying a variety of important problems including understanding and treating diseases, disease-gene associations, and finding appropriate drugs to treat diseases. If two diseases are similar based on a similarity score, then a treatment which works on one disease may also work on the second disease.

A variety of disease similarity metrics have been proposed. Semantic-based similarity considers the structure of a known disease taxonomy structure such as Disease Ontology.

Disease similarity may be based on phenotypes, which are observable characteristics of an organism arising from its response to the environment. Other methods may be used for disease similarity metrics (e.g., gene-based similarity, comorbidity-based similarity).

Disease similarity may be estimated by utilizing one or more factors (e.g., proximity in a disease taxonomy, genes, phenotypes, comorbidity). Disease similarity metrics might be beneficial when determining reasonable treatment choices for different diseases based on how similar the diseases are. If two diseases have a high similarity score, then similar treatments may work for both diseases.

Therefore, it may be advantageous to, among other things, include bioinformatics calculations for disease similarities so that potential treatments (e.g., if a drug may be a good treatment choice for a specific disease, the same treatment choice may be beneficial to other similar diseases) may be identified and utilized for similar diseases.

According to at least one embodiment, the combined disease similarity metrics program may utilize and combine existing disease similarity metrics into more powerful ensemble prediction methodologies. The present embodiment may utilize, as input, one or more disease similarity metrics.

According to at least one embodiment, the combined disease similarity metrics program may obtain a ground truth data set related to diseases that represents correlations between diseases and genes, for example. Disease similarity metrics may be utilized to predict data in the ground truth data set (e.g., if such data is used as training data to develop a model) and linear regression and/or other techniques may be utilized to determine an optimal method for combining disease similarity metrics. The optimized method that may include the combined disease similarity metrics may then be utilized to provide a variety of predictive capabilities, including recommendations for treatments of similar diseases based on the disease similarity. As such, the present embodiment may include algorithms associated with data analytics involving diseases, as well as a wide variety of other data analytics applications involving similarities.

According to at least one embodiment, the combined disease similarity metrics program may also utilize, as input, one or more ground truth data sets (e.g., a ground truth data set may include information on the correlation between diseases and genes, and/or about diseases and drugs which are effective in curing diseases) associated with at least one existing disease.

According to at least one embodiment, the combined disease similarity metrics program may utilize at least one disease similarity metric to predict new associations from existing associations. For example, suppose that a person with gene gene1 has an elevated probability of contracting a disease dis1. If disease dis2 is similar to disease dis1, then a person with gene gene1 might also have an elevated probability of contracting disease dis2. In contrast, if disease dis3 is dissimilar to disease dis1, then a person with gene gene1 may not have an elevated probability of contracting disease dis3. Therefore, the combined disease similarity metrics program may provide a method for inferring new associations from existing associations.

According to at least one embodiment, the combined disease similarity metrics program may be utilized for disease similarity metrics using multiple disease naming conventions (e.g., Unified Medical Language System (UMLS) Concept Unique Identifiers, the Online Mendelian Inheritance in Man (OMIM), the International Classification of Diseases (ICD-9), the Systemized Nomenclature of Medicine (SNOMED) clinical terms, the National Cancer Institute (NCI) Disease Codes, and the Disease Ontology). The combined disease similarity metrics program may select a common disease naming convention and may convert the disease similarity metrics to utilize the same disease naming convention.

According to at least one embodiment, the combined disease similarity metrics program may combine multiple ground truth data sets into a single larger data set. Alternatively, according to another embodiment, the combined disease similarity metrics program may separately analyze each ground truth data set, when multiple ground truth data sets are present. For example, G1 is a ground truth data set used in the analysis (G1 may or may not have been created by merging multiple ground truth data sets) and there are dis1, . . . , disn disease similarity metrics for n>1. The data in G1 is pre-processed, which may remove outliers and anomalous values, as well as impute missing values. The combined disease similarity metrics program may provide multiple methods for imputing missing values including: (a) average value from a set of values; (b) median value from a set of values; (c) most frequently occurring value from a set of values; and (d) using collaborative filtering techniques for data in G.

The present embodiment may include at least one collaborative filtering technique, which may include matrix factorization.

According to at least one embodiment, the combined disease similarity metrics program, after pre-processing, may select at least one training set tr1 from G1 and at least one test set te1 from G1 (e.g., te1 may be distinct from tr1) for each disease similarity metric di. For example, suppose G1 includes data indicating the likelihood of a correlation between a disease dis1 and a gene gene1. A higher value of G1(dis1, gene1) may indicate a higher probability a person with gene1 has of contracting disease dis1. A lower value of G1(dis1, gene1) may indicate a lower probability a person with gene1 has of contracting disease dis1. Training data tr1 may include disease, gene pairs (dis1, gene1) along with values of G1(dis1, gene1). The test set te1 may include disease, gene pairs (dis2, gene2) without the values of G1(dis2, gene2).

According to at least one embodiment, the combined disease similarity metrics program may predict values of G1 for disease, gene pairs in te1 from the data in tr1. To compute, for example, G1(dis2, gene2) from data in tr1, the combined disease similarity metrics program may utilize di(dis1, dis2) as a similarity metric indicating the degree of similarity between diseases dis1 and dis2. A higher value may indicate a higher degree of similarity. The combined disease similarity metrics program may also normalize the similarity metric for the values of di to be between 0 (least similarity) and 1 (most similarity).

The combined disease similarity metrics program may, for example, utilize di to infer a value of G1(dis2, gene2). For one or more G1(dis_a, gene_a) in te1, the combined disease similarity metrics program may find one or more diseases dis_b for which: (1) G1 (dis_b, gene_a) is in tr1; and (2) di(dis_a, dis_b)>=t, for a threshold similarity t (t can be 0 or nonzero). If any such dis_b exists, the combined disease similarity metrics program may predict, for example, that:

$$G1(dis\_a, gene\_a) = \text{average of } G1(dis\_b, gene\_a) \text{ weighted by } di(dis\_a, dis\_b) \quad \text{Formula 1:}$$

The combined disease similarity metrics program utilizes the above Formula 1 by preferably, but not necessarily, considering all dis_b satisfying (1) and (2).

The present embodiment may refer to each disease dis_b utilized to predict G1 (dis_a, gene_a) using di as a di-predictive disease for G1(dis_a, gene_a). If, however, within the present embodiment, no dis_b exists, G1(dis_a, gene_a)

is assigned a default value by the combined disease similarity metrics program, such as an average of:

G1(dis_e,gene_e) for the pairs (dis_e,gene_e) in tr1

The present embodiment may include predicting values for disease, gene pairs in te1, and setting a value for t. The combined disease similarity metrics program may further optimize predictions (i.e., maximize prediction accuracy) by considering several values of t. For each value of t, the combined disease similarity metrics program may determine the accuracy of predictions of G1 values for disease, gene pairs in te1. The combined disease similarity metrics program may select an optimal value of t as a value that maximizes the accuracy of G1 predictions for te1.

According to at least one embodiment, the combined disease similarity metrics program may utilize one or more metrics for determining accuracy of predictions, including: (1) a sum of squares of differences between each predicted value and each actual value in which the lower numbers represent higher accuracy; and (2) a sum of absolute values of differences between each predicted value and each actual value in which the lower numbers represent higher accuracy.

According to at least one embodiment, the combined disease similarity metrics program may generate additional candidates for predicting G1 (dis2, gene2) by considering similarities between genes. For example, suppose that Q1(gene1, gene2) provides a quantitative measure of similarity (Q1) between genes (where gene1 and gene2 may range over different genes). We can then predict G1(dis2, gene2) from pairs (dis2, gene2) most similar to (dis2, gene2). As such, the combined disease similarity metrics program may utilize a metric to compute similarity between pairs of diseases and genes, and not solely compute the similarity between diseases and between genes. Such a metric is given by:

sim_i((dis2,gene2),(dis3,gene3))=avg(di(dis2,dis3), Q1(gene2,gene3))

In the above metric, avg may, for example, calculate the geometric mean of the di and Q1 values, harmonic mean of these values, arithmetic mean of these values, or some other type of average value. To predict G1(dis2, gene2), the combined disease similarity metrics program may, for example, for one or more G1 (dis_a, gene_a) in te1, find one or more disease, gene pairs (dis_b, gene_b) for which (1) G1 (dis_b, gene_b) is in tr1 and (2) sim_i((dis_a, gene_a), (dis_b, gene_b))>=t2, for a threshold similarity t2 (t2 can be 0 or nonzero). If any such (dis_b, gene_b) exists, the combined disease similarity metrics program may predict that:

G1(dis_a,gene_a)=average of G1(dis_b,gene_b) weighted by sim_i((dis_a,gene_a),(dis_b, gene_b))   Formula 2

The combined disease similarity metrics program utilizes the above Formula 2 by preferably, but not necessarily, considering all (dis_b, gene_b) satisfying (1) and (2).

The present embodiment may then refer to each pair (dis_b, gene_b) utilized to predict G1(dis_a, gene_a) using sim_i as a sim_i-predictive pair for G1(dis_a, gene_a). If, however, within the present embodiment, no (dis_b, gene_b) exists, G1(dis_a, gene_a) may be assigned a default value by the combined disease similarity metrics program, such as an average of:

G1(dis_e,gene_e) for pairs (dis_e,gene_e) in tr1

According to at least one embodiment, the combined disease similarity metrics program may utilize the above method to predict values for disease, gene pairs in te1. The method requires setting a value for t2. The combined disease similarity metrics program may further optimize predictions by considering several values of t2. For each value of t2, the combined disease similarity metrics program may determine the accuracy of predictions of G1 values for disease, gene pairs in te1. The combined disease similarity metrics program may select an optimal value of t2 as a value that maximizes the accuracy of G1 predictions for te1. As previously described, the combined disease similarity metrics program may utilize one or more metrics for determining accuracy of predictions.

According to at least one embodiment, the combined disease similarity metrics program may utilize the above methods for predicting gene-disease associations using more than one disease similarity metric. If there are n disease similarity metrics, then the combined disease similarity metrics program may include a different prediction for G1 (dis_a, gene_a) resulting from each disease similarity metric. The combined disease similarity metrics program may combine the different predictions to result in a better prediction as opposed to a single disease similarity metric. The present embodiment may further include the use of multiple linear regression with the G1 values as the dependent variable and the predictions for G1 using each of the disease similarity metrics as the independent (explanatory) variables to predict gene-disease associations using more than one disease similarity metric. Additionally, a wide variety of other techniques (e.g., random forests, gradient boosted trees, neural networks, several others) may also be used to generate an ensemble predictor for disease-gene associations from a plurality of individual predictors of disease-gene associations.

According to at least one embodiment, one or more models generated by the combined disease similarity metrics program in which the above described methods are utilized may be applied to predict disease-gene associations for disease, gene pairs outside of the ground truth G1. Since merely a fraction of possible disease-gene associations include in depth study, many possible disease-gene associations may be unknown. In addition to providing a new method for determining disease similarities, the combined disease similarity metrics program may provide new methods for predicting such associations that are unknown.

According to at least one embodiment, the combined disease similarity metrics program may provide at least one method for explaining, to users, how a prediction is obtained. Suppose, for example, the combined disease similarity metrics program makes a prediction for an association between gene gene1 and disease dis1. The association may be based on identifying at least one disease dis_b such that (1) G1(dis_b, gene1) is in tr1 and (2) di(dis1, dis_b)>, t, for a disease similarity metric di and threshold similarity t. The combined disease similarity metrics program may further explain the prediction for the association between gene1 and dis1 by providing one or more diseases dis_b used in the calculation, G1(dis_b, gene1), di(dis1, dis_b), and/or the threshold t.

According to at least one embodiment, the prediction may, alternatively or additionally, be based on identifying at least one disease, gene pair (dis_b, gene_b) such that (1) G1(dis_b, gene_b) is in tr1 and (2) sim_i((dis1, gene1), (dis_b, gene_b))>=t2, for a threshold similarity t2. The combined disease similarity metrics program may explain the prediction for the association between gene1 and dis1 by providing one or more disease-gene pairs (dis_b, gene_b)

used in the calculation, G1(dis_b, gene_b), sim_i((dis1, gene1), (dis_b, gene_b)), and/or the threshold t2.

According to at least one embodiment, if the prediction was made by using multiple disease similarity scores, the combined disease similarity metrics program may provide specific predictions from each individual disease similarity score as all or part of the explanation.

According to at least one embodiment, the combined disease similarity metrics program may provide methods to estimate the accuracy of a prediction, since the users may also request the accuracy of a prediction. For example, suppose that the combined disease similarity metrics program includes a prediction for an association between gene gene_a and disease dis_a. The combined disease similarity metrics program may denote this prediction (P1) by P1(dis_a, gene_a). The accuracy of the prediction may be higher if more predictive diseases and/or predictive pairs are utilized to calculate the prediction, if more disease similarity metrics are utilized to calculate the prediction, and/or if there is less variance in the G1 values corresponding to predictive diseases and/or predictive pairs utilized to calculate the prediction. The combined disease similarity metrics program may construct an accuracy determination model m2 to predict the accuracy of predictions which includes one or more of the following as input parameters, where P1(dis_a, gene_a), for example, is the value being predicted:

(1) number of predictive diseases used to obtain the prediction;

(2) over disease similarity metrics di used to obtain the prediction and each di-predictive disease dis_b, the sum of di(dis_a, dis_b);

(3) number of predictive pairs used to obtain the prediction;

(4) over sim_i used to obtain the prediction and each simi-predictive pair (dis_b, gene_b), the sum of sim_i ((dis_a, gene_a), (dis_b, gene_b));

(5) number of disease similarity metrics used to obtain the prediction;

(6) the variance of G1 values used to obtain the prediction using Formula 1 and/or Formula 2;

(7) the standard deviation of G1 values used to obtain the prediction using Formula 1 and/or Formula 2;

(8) the weighted variance of G1 values used to obtain the prediction using Formula 1 and/or Formula 2; and (9) the weighted standard deviation of G1 values used to make the prediction using Formula 1 and/or Formula 2.

According to at least one embodiment, the variance (mentioned in above (6) and (8)) may be computed by taking the difference of each data point and the average, squaring this difference, summing the squared values, and then dividing by either n or n−1, where n is the number of data points. Note that the present embodiment may use standard definitions of variance and standard deviation commonly taught in statistics courses. The combined disease similarity metrics program may define the weighted variance of the G1 values used to obtain the prediction using Formula 1 or Formula 2 utilizing a similar formula as conventional variance, and multiplying the difference of each data point and the average by:

di(dis_a, dis_b) for Formula 1 predictions.

sim_i((dis_a, gene_a), (dis_b, gene_b)) for Formula 2 predictions.

In the present embodiment, the combined disease similarity metrics program may compute that the weighted standard deviation is the square root of the weighted variance.

According to at least one embodiment, in order to estimate accuracy of a predictive model m1 for disease-gene associations, the combined disease similarity metrics program may utilize m1 to calculate disease-gene associations for a set of disease, gene pairs S, whose values are known. The combined disease similarity metrics program may then determine a set of error values E comprised of the differences between the actual values for pairs in S and the predicted values for pairs in S. The combined disease similarity metrics program may train the accuracy determination model m2 using E as a training set. The combined disease similarity metrics program may optionally tune m2 using other data. Model m2 may then be used to predict error values for predictive model m1.

The combined disease similarity metrics program may calculate ensemble disease similarity metrics based on multiple disease similarity metrics as described below.

According to at least one embodiment, if multiple linear regression is used to determine G1 from a plurality of disease similarity metrics, the combined disease similarity metrics program may utilize the linear regression coefficients to define an ensemble disease similarity metric. The ensemble disease similarity metric for a pair of diseases dis1 and dis2 may be the sum (over disease similarity metrics di) of ai*di(dis1, dis2), where ai is the linear regression coefficient for the prediction of G1 resulting from di. The combined disease similarity metrics program may optionally normalize the ensemble disease similarity metric so that the values may range from a low of 0 to a high of 1.

This approach may be generalized to multiple ground truth data sets G1, G2, . . . , Gm. According to at least one embodiment, the combined disease similarity metrics program may apply the above process of calculating an ensemble disease similarity metric for a ground truth data set by associating a regression coefficient ai with each metric di for m ground truth data sets (where m>1) resulting in m regression coefficients for di, one for each ground truth data set. Let ai_sum be the sum of these m regression coefficients. The ensemble disease similarity metric for a pair of diseases dis1 and dis2 may be the sum or addition of a plurality of products (over disease similarity metrics di) of ai_sum*di (dis1, dis2). The combined disease similarity metrics program may optionally normalize the ensemble disease similarity metric so that the values may range from a low of 0 to a high of 1.

According to at least one embodiment, a variation on this approach may be to have ai_sum be a weighted sum of the m regression coefficients, where a weight associated with a coefficient is correlated with how important the corresponding ground truth data set is. Therefore, the combined disease similarity metrics program may give some ground truth data sets more weight in determining the ensemble similarity metric than others.

In the present embodiment, a variation on the above approach for calculating ensemble disease similarity metrics based on multiple disease similarity metrics is to use other forms of regression besides multiple linear regression. For example, a nonlinear regression method can be used instead of linear regression for determining G1 and for determining one or more combined disease similarity metrics.

The methods, systems and/or computer program products described above may be applicable for similarity metrics of other types of entities and not just diseases. For example, the methods described above can be applied to similarity metrics of genes, proteins, drugs, movies, companies, etc.

Referring to FIG. 1, an exemplary networked computer environment 100 in accordance with one embodiment is depicted. The networked computer environment 100 may include a computer 102 with a processor 104 and a data storage device 106 that is enabled to run a software program 108 and a combined disease similarity metrics program 110a. The networked computer environment 100 may also include a server 112 that is enabled to run a combined disease similarity metrics program 110b that may interact with a database 114 and a communication network 116. The networked computer environment 100 may include a plurality of computers 102 and servers 112, only one of which is shown. The communication network 116 may include various types of communication networks, such as a wide area network (WAN), local area network (LAN), a telecommunication network, a wireless network, a public switched network and/or a satellite network. It should be appreciated that FIG. 1 provides only an illustration of one implementation and does not imply any limitations with regard to the environments in which different embodiments may be implemented. Many modifications to the depicted environments may be made based on design and implementation requirements.

The client computer 102 may communicate with the server computer 112 via the communications network 116. The communications network 116 may include connections, such as wire, wireless communication links, or fiber optic cables. As will be discussed with reference to FIG. 6, server computer 112 may include internal components 902a and external components 904a, respectively, and client computer 102 may include internal components 902b and external components 904b, respectively. Server computer 112 may also operate in a cloud computing service model, such as Software as a Service (SaaS), Analytics as a Service (AaaS), Platform as a Service (PaaS), or Infrastructure as a Service (IaaS). Server 112 may also be located in a cloud computing deployment model, such as a private cloud, community cloud, public cloud, or hybrid cloud. Client computer 102 may be, for example, a mobile device, a telephone, a personal digital assistant, a netbook, a laptop computer, a tablet computer, a desktop computer, or any type of computing devices capable of running a program, accessing a network, and accessing a database 114. According to various implementations of the present embodiment, the combined disease similarity metrics program 110a, 110b may interact with a database 114 that may be embedded in various storage devices, such as, but not limited to a computer/mobile device 102, a networked server 112, or a cloud storage service.

According to the present embodiment, a user using a client computer 102 or a server computer 112 may use the combined disease similarity metrics program 110a, 110b (respectively) to use disease similarity metrics to make predictions. The combined disease similarity metrics method is explained in more detail below with respect to FIGS. 2-5.

Figure 2:
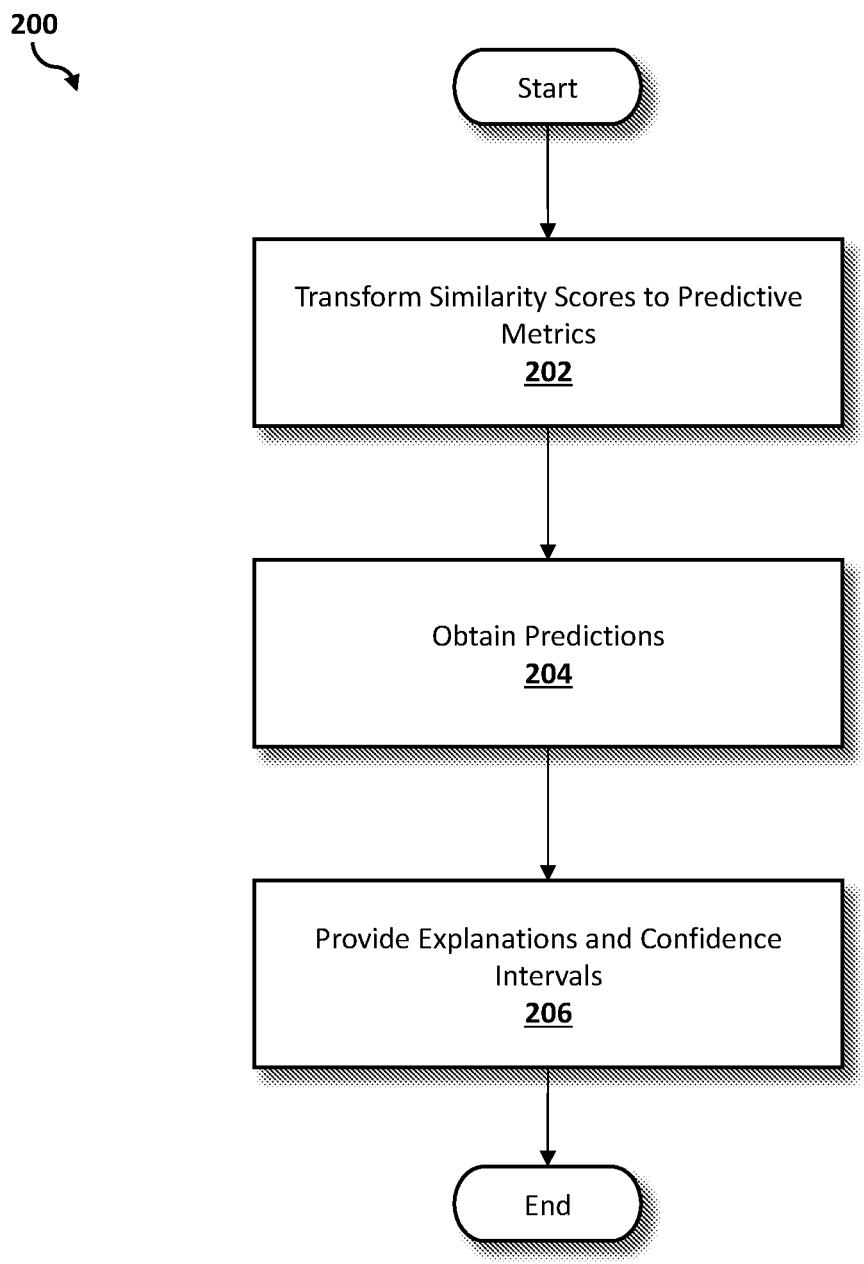
FIG. 2 is an operational flowchart illustrating a process for utilizing multiple similarity metrics to make predictions according to at least one embodiment.

Referring now to FIG. 2, an operational flowchart illustrating the exemplary disease similarity metrics utilization data analysis process 200 used by the combined disease similarity metrics program 110a, 110b to make predictions according to at least one embodiment is depicted.

At 202, at least one similarity score is transformed to predictive metrics. The combined disease similarity metrics program 110a, 110b may obtain a ground truth data set related to diseases and genes, which specifies correlations between diseases and genes. Various types of disease similarity scores may be employed to identify similarities between diseases. For example, DisSim is the disease similarity metric, DisGeNet provides disease-gene associations and disease similarity metrics, and phonotype-based disease similarity metrics.

In another embodiment, using a software program 108 on a user device (e.g., user's computer 102), the disease similarity scores and/or the ground truth data set may be entered or uploaded, as input, into the combined disease similarity metrics program 110a, 110b via communication network 116.

Then, at 204, predictions are obtained. The combined disease similarity metrics program 110a, 110b may utilize each disease similarity metric to predict data in the ground truth data set. For example, in one illustrative embodiment, a subset of disease-gene associations from the DisGeNet ground truth data set is used for training, where these disease-gene associations include a correlation of probabilities that there is a link between a gene gene1 and a disease dis1 for P1(gene1, dis1). The different disease similarity metrics (s1, s2, s3) (i.e., a metric quantifying similarity of entities belong to the first or second data type) may be utilized to predict the disease-gene associations of the ground truth data set. As such, the combined disease similarity metrics program 110a, 110b may modify and adjust the disease-similarity algorithms through training.

Additionally, the combined disease similarity metrics program 110a, 110b may assign weights to the particular similarity metrics and utilize linear regression techniques to determine the way to combine the similarity metrics. The combined disease similarity metrics program 110a, 110b may, for example, obtain the predictions by:

(1) Correlating with probability that there is a link between gene gene1 and disease dis1 (i.e., P1(gene1, dis1));

(2) Determining the similarity between disease dis1 and dis2 (value between 0 and 1) (i.e., s1(dis1, dis2));

(3) Utilizing s1 to infer new P1 values from P1 values in training set;

(4) Dividing P1 into training set and test set in which the user specifies proportion of data for each set;

(5) For each P1(gene1, dis1) in the test set, the combined disease similarity metrics program 110a, 110b may find the diseases disj for which (a) P1(gene1, disj) is in training set, and (2) s1 (dis, disj)>=t, for a threshold similarity t (t may be 0);

(6) Determining whether disj exists. If the combined disease similarity metrics program 110a, 110b determines that disj exists, P1'(gene1, dis1)=average of P1(gene1, disj) may be weighted by s1(dis1, disj). If, however, the combined disease similarity metrics program 110a, 110b determines that no disj exists, P1'(gene1, dis1)=average P1(gene1, dis1) for P1(gene1, dis1) in training set. The t may be varied to determine the most accurate P1' prediction for P1 associated with the training set;

(7) Generating candidates for predicting P1(gene1, dis1) by considering similarities in diseases and not in genes;

(8) Generating additional candidates for predicting P1(gene1, dis1) by considering similarities between genes;

(9) Determining the similarity between gene gene1 and gene2 (value between 0 and 1) (i.e., t1(gene1, gene2));

(10) Predicting P1(gene1, dis1) from pairs (genej, disj) which are most similar to (gene1, dis1); and

(11) Determining the similarity ((gene1, dis1), (gene2, dis2))=avg (s1(dis1, dis2), t1(gene1, gene2)), where the avg may be geometric or harmonic mean.

In the present embodiment, the combined disease similarity metrics program 110a, 110b may utilize the above method for predicting disease-gene associations for each metric, and linear regression may be utilized to determine an optimal way to use metrics in predictions.

Then, at 206, at least one explanation and at least one confidence interval are provided. The combined disease similarity metrics program 110a, 110b may provide explanations of the prediction for P1(gene1, dis1) based on the relative weights of similarity scores from a regression analysis. Continuing the previous example, that is, for each similarity score s1 used in a prediction, the values of P1(gene1, dis2), where P1(gene1, dis2) is known and s1(dis1, dis1)>=t may be provided.

Additionally, the combined disease similarity metrics program 110a, 110b may assign a confidence interval to the range of probability scores (e.g., probability (0.1<P1(gene1, dis1)<0.3)=0.9). The confidence interval may be correlated with the degree of agreement for different predictive metrics and the confidence in predictions for a single similarity score s1 correlated with similarities in values of P1(gene1, dis2) where P1(gene1, dis2) is known and s1 (dis1, dis2)>=t.

For example, users are often interested both in the explanations of why a certain prediction is made and how accurate the prediction is. The combined disease similarity metrics program provides both characteristics. Predictions, such as disease-gene correlations, may be made by the combined disease similarity metrics program, along with explanations of key factors resulting in the prediction and how much error is associated with the prediction.

In another embodiment, the user may enter or choose to upload the values (e.g., disease similarity scores, ground truth data sets) into the combined disease similarity metrics program 110a, 110b, and the combined disease similarity metrics program 110a, 110b may generate an output (e.g., predictions, explanations and confidence intervals) via a user device (e.g., user's computer 102).

In another embodiment, the user may provide feedback on the output generated by the combined disease similarity metrics program 110a, 110b. As such, the user may improve the quality of the output (e.g., predictions, explanations, error estimations, data models, enhanced similarity scores) generated by the combined disease similarity metrics program 110a, 110b. The user may provide feedback by clicking on a "User Feedback" button located on the bottom right side of the screen connected to the user device operating the combined disease similarity metrics program 110a, 110b. Once the user clicks on the "User Feedback" button, the user may be prompted (e.g., via first dialog box) to indicate the output that the user feedback is associated with. In the list of output options, there may be a button associated with each of the output options (e.g., "Predictions," button, "Data Models" button, "Explanations" button, "Error Estimation" button, "Enhanced Similarity Scores" button). If the user clicks the one of the buttons in the first dialog box, then the first dialog box may expand the list of recent outputs associated with the selected output option (e.g., if the "Data Models" button is selected, then a list of the thirty most recent data models may be presented for the user). Each recent output may include a button to the left in which the user may click to select that recent output. Once the user selects a recent output, the user may be prompted, (e.g., via second dialog box) to provide feedback on the selected recent output. The user may provide a written feedback in the comment box located in the center of the second dialog box, and may click the "Submit" button located directly under the comment box. The user may then be prompted (e.g., via third dialog box) whether the user intends to provide additional feedback associated with another recent output by clicking the "Yes" or "No" buttons in the third dialog box. Once the user clicks "No," the first, second, and third dialog box may disappear. If, however, the user selects the "Yes" button, then the user will return to the first dialog box to indicate the output that the user feedback is associated with.

In another embodiment, the user may configure the number of recent outputs included when providing user feedback by clicking on a "Settings" button located on the bottom center of the screen connected to the user device operating the combined disease similarity metrics program 110a, 110b. Once the user clicks on the "Settings" button, the user may be prompted (e.g., via dialog box) to indicate the setting that the user intends to change. In the list of settings, there may be a "Number of Recent Outputs" button. If the user clicks the "Number of Recent Outputs" button, then the dialog box may expand the list of possible number of recent outputs ranging from five to fifty recent outputs in increments of five. The user may select the preferred number of recent outputs. The dialog box may expand and prompt the user to confirm the preferred number of recent outputs by clicking the "Yes" or "No" button under a statement restating the preferred number of recent outputs. Once the user clicks "Yes," the dialog box may disappear. If, however, the user selects the "No" button, then the dialog box may remain for the user to clarify the preferred number of recent outputs.

In another embodiment, the output generated by the combined disease similarity metrics program 110a, 110b (e.g., predictions, explanations and confidence intervals) may be stored in a database (e.g., database 114) for future access and may be used to improve the function of the combined disease similarity metrics program 110a, 110b operated by the user device (e.g., user's computer 102). For example, the combined disease similarity metrics program 110a, 110b may utilize the stored output or data in the database, when making a new prediction, or generating a new explanation or confidence intervals. The database may be indexed, for example, by the type of genes and diseases that are associated with the output. Additionally, the user may be able to configure the database associated with the combined disease similarity metrics program 110a, 110b to index based on different variables (e.g., highest to lowest similarity scores, highest to lowest confidence intervals).

Figure 3:
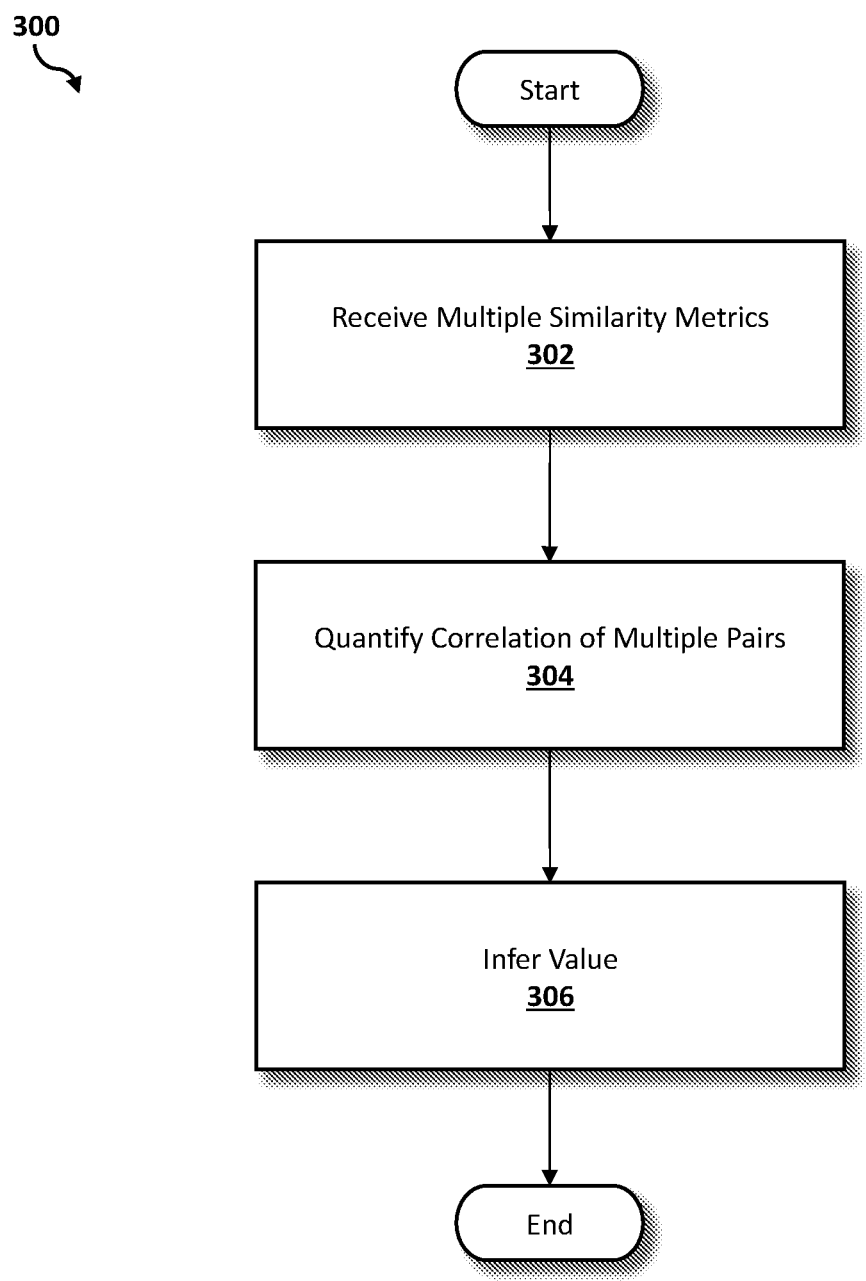
FIG. 3 is an operational flowchart illustrating a process for analyzing data belonging to a plurality of data types according to at least one embodiment.

Referring now to FIG. 3, an operational flowchart illustrating the exemplary data analysis process 300 for data belonging to a plurality of data types used by the combined disease similarity metrics program 110a, 110b according to at least one embodiment is depicted.

As shown, at 302, multiple similarity metrics are received, and then, at 304, a correlation of multiple pairs is quantified. After receiving and preprocessing the data, the combined disease similarity metrics program 110a, 110b may search the data to locate at least one piece of data that may indicate the likelihood of correlation between the disease dis1 and a gene gene1 (i.e., pair of entities), thereby computing a similarity metric for a pair of entities (or multiple similarity metrics for multiple pairs of entities (i.e., the first data type comprises diseases and the second data type comprises genes)). Therefore, the combined disease similarity metrics program 110a, 110b may select at least one training set tr1 from G1 and at least one test set te1 from G1 (e.g., te1 may be distinct from tr1) for each disease similarity metric di. A higher value of G1(dis1, gene1) may indicate a higher probability a person with gene1 has of contracting disease dis1. A lower value of G1(dis1, gene1) may indicate a lower probability a person with gene1 has of contracting disease dis1. Training data tr1 may include disease, gene pairs (dis1, gene1) along with values of G1(dis1, gene1). The test set te1 may include disease, gene pairs (dis2, gene2) without the values of G1(dis2, gene2).

The combined disease similarity metrics program 110a, 110b may then predict values of G1 for disease, gene pairs in te1 from the data in tr1. To compute, for example, G1(dis2, gene2) from data in tr1, the combined disease similarity metrics program 110a, 110b may utilize di(dis1, dis2) as a similarity metric indicating the degree of similarity between diseases dis1 and dis2. A higher value may indicate a higher degree of similarity. The combined disease similarity metrics program 110a, 110b may also normalize the similarity metric for the values of di to be between 0 (least similarity) and 1 (most similarity).

In another embodiment, using a software program 108 on a user device (e.g., user's computer 102), the multiple disease similarity metrics may be entered or uploaded, as input, into the combined disease similarity metrics program 110a, 110b via communication network 116.

Then, at 306, a value is inferred. The combined disease similarity metrics program 110a, 110b may run a predictive algorithm to infer known values of a metric quantifying correlation of entities belonging to the first data type and entities belonging to the second data type (c1) (e.g., G1(dis2, gene2)) multiple times using different values for threshold (t1). The combined disease similarity metrics program 110a, 110b may, for example, utilize di to infer a value of G1(dis2, gene2) (i.e., cl(b1, b2), cl(b3, b4)). For one or more G1(dis_a, gene_a) in te1, the combined disease similarity metrics program 110a, 110b may find one or more diseases dis_b in which: (1) G1(dis_b, gene_a) is in tr1; and (2) di(dis_a, dis_b)>=t (i.e., s1(b3,e1)), for a threshold similarity t (t can be 0 or nonzero). If dis_b exists, the combined disease similarity metrics program 110a, 110b may predict, for example, that:

$$G1(dis\_a, gene\_a) = \text{average of } G1(dis\_b, gene\_a) \quad \text{Formula 1}$$

Additionally, the combined disease similarity metrics program 110a, 110b may preferably utilize the above Formula 1, without necessarily considering all dis_b satisfying (1) and (2) weighted by di(dis_a, dis_b).

The present embodiment may refer to each disease dis_b utilized to predict G1 (dis_a, gene_a) using di as a predictive disease for G1(dis_a, gene_a). If, however, within the present embodiment, no dis_b exists, G1(dis_a, gene_a) may be assigned a default value by the combined disease similarity metrics program 110a, 110b, such as an average of:

$$G1(dis\_e, gene\_e) \text{ for the pairs } (dis\_e, gene\_e) \text{ in } tr1$$

Additionally, the combined disease similarity metrics program 110a, 110b may include predicting values for disease, gene pairs in te1, and setting a value for t. The combined disease similarity metrics program 110a, 110b may further optimize predictions (i.e., maximize prediction accuracy) by considering several values of t. For each value of t, the combined disease similarity metrics program 110a, 110b may determine the accuracy of predictions of G1 values for disease, gene pairs in te1. The combined disease similarity metrics program 110a, 110b may select an optimal value of t as a value that maximizes the accuracy of G1 predictions for te1. A detailed operational flowchart of the error estimation process in the combined disease similarity metrics program 110a, 110b will be described in greater detail below with respect to FIG. 5.

In another embodiment, the combined disease similarity metrics program 110a, 110b may utilize multiple metrics for determining accuracy of predictions (e.g., a sum of squares of differences between each predicted value and each actual value in which the lower numbers represent higher accuracy, a sum of absolute values of differences between each predicted value and each actual value in which the lower numbers represent higher accuracy).

In another embodiment, the combined disease similarity metrics program 110a, 110b may generate additional candidates for predicting G1 (dis2, gene2) by considering similarities between genes. For example, suppose that Q1(gene1, gene2) provides a quantitative measure of similarity (Q1) between genes (where gene1 and gene2 may range over different genes). We can then predict G1(dis2, gene2) from pairs (dis3, gene3) most similar to (dis2, gene2). As such, the combined disease similarity metrics program 110a, 110b may utilize a metric to compute similarity between pairs of diseases and genes (i.e., a third metric quantifying similarity of pairs of entities), and not solely compute the similarity between diseases and between genes. Such a metric is given by:

$$\text{sim}\_i((dis2, gene2), (dis3, gene3)) = \text{avg}(di(dis2, dis3), Q1(gene2, gene3))$$

In the above metric, avg may, for example, calculate the geometric mean of the di and Q1 values (e.g., s1(a1, a2) and s2(q1, q2)), harmonic mean of these values, or arithmetic mean of these values. To predict G1(dis2, gene2), the combined disease similarity metrics program 110a, 110b may, for example, for one or more G1(dis_a, gene_a) in te1, find one or more disease, gene pairs (dis_b, gene_b) for which (1) G1(dis_b, gene_b) is in tr1 and (2) sim_i((dis_a, gene_a), (dis_b, gene_b))>=t2 (i.e., sim1((b3,c4), (ei, ej))), for a threshold similarity t2 (t2 can be 0 or nonzero). If (dis_b, gene_b) exists, the combined disease similarity metrics program 110a, 110b may predict that:

$$G1(dis\_a, gene\_a) = \text{average of } G1(dis\_b, gene\_b) \quad \text{Formula 2}$$

The combined disease similarity metrics program 110a, 110b may preferably utilize the above Formula 2, without necessarily considering (dis_b, gene_b) satisfying (1) and (2) weighted by sim_i((dis_a, gene_a), (dis_b, gene_b)).

The combined disease similarity metrics program 110a, 110b may then refer to each pair (dis_b, gene_b) utilized to predict G1(dis_a, gene_a) using sim_i as a sim_i-predictive pair for G1(dis_a, gene_a). If, however, within the present embodiment, no (dis_b, gene_b) exists, G1(dis_a, gene_a) may be assigned a default value by the combined disease similarity metrics program 110a, 110b, such as an average of:

$$G1(dis\_e, gene\_e) \text{ for pairs } (dis\_e, gene\_e) \text{ in } tr1$$

The combined disease similarity metrics program 110a, 110b may further utilize the above method to predict values for disease, gene pairs in te1, and setting a value for t2. The combined disease similarity metrics program 110a, 110b may further optimize predictions by considering several values of t2. For each value of t2, the combined disease similarity metrics program 110a, 110b may determine the accuracy of predictions of G1 values for disease, gene pairs in te1. The combined disease similarity metrics program 110a, 110b may select an optimal value of t2 as a value that maximizes the accuracy of G1 predictions for te1. A detailed operational flowchart of the error estimation process in the combined disease similarity metrics program 110a, 110b will be described in greater detail below with respect to FIG. 5.

The combined disease similarity metrics program 110a, 110b may predict accurate values for disease-gene associations. By making predictions with multiple values of t, the combined disease similarity metrics program 110a, 110b may be able to select a value of t resulting in the best predictions.

In another embodiment, the output generated by the combined disease similarity metrics program 110a, 110b (e.g., multiple similarity metrics, quantified correlation of multiple pairs and inferred value) may be stored in a database (e.g., database 114) for future access and may be used to improve the function of the combined disease similarity metrics program 110a, 110b operated by the user device (e.g., user's computer 102). For example, the combined disease similarity metrics program 110a, 110b may utilize the stored output or data in the database when inferring new values. The database may be indexed, for example, by the type of genes and diseases that are associated with the output. Additionally, the user may be able to configure the database associated with the combined disease similarity metrics program 110a, 110b to index based on different variables.

Figure 4:
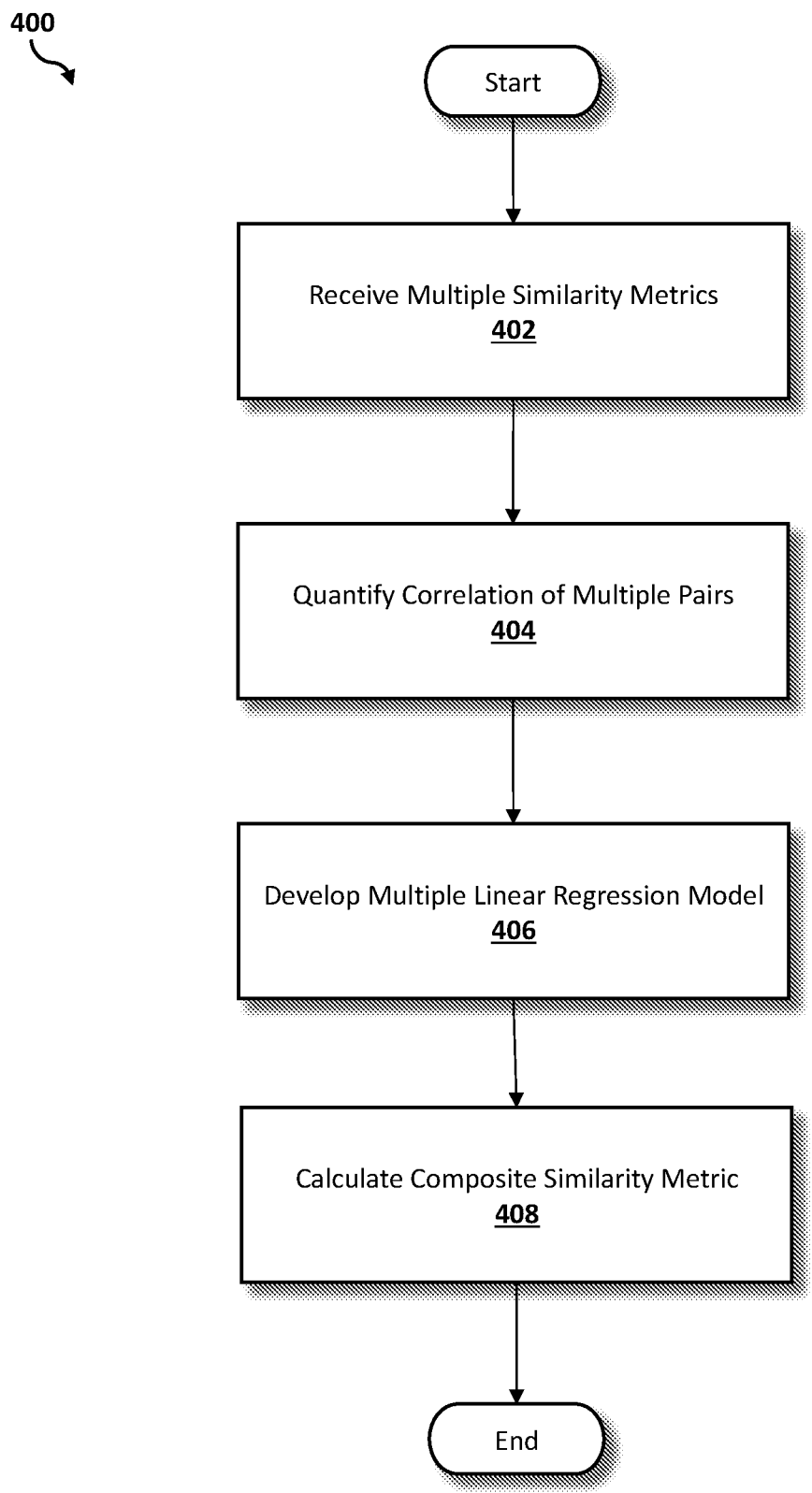
FIG. 4 is an operational flowchart illustrating a process for determining a composite similarity metric for data according to at least one embodiment.

Referring now to FIG. 4, an operational flowchart illustrating the exemplary data composite similarity metric determination process 400 used by the combined disease similarity metrics program 110a, 110b by combining multiple similarity metrics according to at least one embodiment is depicted.

As shown, multiple similarity metrics are received at 402 (i.e., receive multiple similarity metrics 302), and then, at 404, a correlation of multiple pairs is quantified (i.e., quantify correlation of multiple pairs 304). Then, at 406, a multiple linear regression model (i.e., first and second regression models) is developed. The combined disease similarity metrics program 110a, 110b may utilize two or more linear regression coefficients (i.e., first regression coefficients) to define an ensemble disease similarity metric (i.e., composite similarity metric) when multiple linear regression may be developed to determine G1 from the disease similarity metrics. The multiple linear regression model may further predict c1 values by utilizing multiple similarity metrics for each ground truth data set (i.e., second regression model). The ensemble disease similarity metric for a pair of diseases dis1 and dis2 may then be considered the sum (over disease similarity metrics di) of ai*di(dis1, dis2), where ai is the linear regression coefficient for the prediction of G1 resulting from di. As such, the ensemble disease similarity metric may be calculated by adding linear regression coefficients corresponding to models in different ground truth data sets (i.e., second regression coefficients).

In the present embodiment, the ensemble disease similarity metric may be calculated by adding linear regression coefficients corresponding to models in different ground truth data sets weighted by the importance of the ground truth data set(i.e., second regression coefficients). For example, a variation may be utilized in which the ai_sum may be a weighted sum of the m regression coefficients, and a weight associated with a coefficient is correlated with the importance of the corresponding ground truth data set. Therefore, some ground truth data sets may be given more weight in determining the ensemble similarity metric as compared to other ground truth data sets. Applying varied weights to the ground truth data sets may be applicable for similarity metrics of other types of entities (e.g., genes, proteins, drugs, movies, companies) and not solely diseases.

In the present embodiment, the combined disease similarity metrics program 110a, 110b may optionally normalize the ensemble disease similarity metric for the values to range from a low of 0 to a high of 1.

Then, at 408, at least one composite similarity metric is calculated. The combined disease similarity metrics program 110a, 110b may generalize the multiple ground truth data sets G1, G2, ..., Gm. The combined disease similarity metrics program 110a, 110b may then present how to calculate an ensemble disease similarity metric (i.e., composite similarity metric) for ground truth data set G1 by associating a regression coefficient ai with each metric di. The combined disease similarity metrics program 110a, 110b may repeat this process for the m ground truth data sets resulting in m regression coefficients for di, one for each ground truth data set, and ai_sum may be the sum of the m regression coefficients. The ensemble disease similarity metric for a pair of diseases dis1 and dis2 may then be the sum (over disease similarity metrics di) of ai_sum*di(dis1, dis2).

In the present embodiment, the combined disease similarity metrics program 110a, 110b may optionally normalize the ensemble disease similarity metric for the values to range from a low of 0 to a high of 1.

The combined disease similarity metrics program 110a, 110b may combine multiple disease similarity metrics to produce a more powerful composite similarity metric. The methods, systems and/or computer program products described above may produce composite disease similarity metrics, which may outperform the individual similarity metrics on which the composite disease similarity metrics are based. Therefore, the combined disease similarity metrics program 110a, 110b may improve the accuracy of bioinformatics calculations, such as predicting disease-gene associations and predicting treatments for diseases.

In another embodiment, the output generated by the combined disease similarity metrics program 110a, 110b (e.g., multiple similarity metrics, quantified correlation of multiple pairs, composite similarity metric, and multiple linear regression model) may be stored in a database (e.g., database 114) for future access and may be used to improve the function of the combined disease similarity metrics program 110a, 110b operated by the user device (e.g., user's computer 102). For example, the combined disease similarity metrics program 110a, 110b may utilize the stored output or data in the database when calculating composite similarity metrics or developing a multiple linear regression model (i.e., data model). The database may be indexed, for example, by the type of genes and diseases that are associated with the output. Additionally, the user may be able to configure the database associated with the combined disease similarity metrics program 110a, 110b to index based on different variables.

Figure 5:
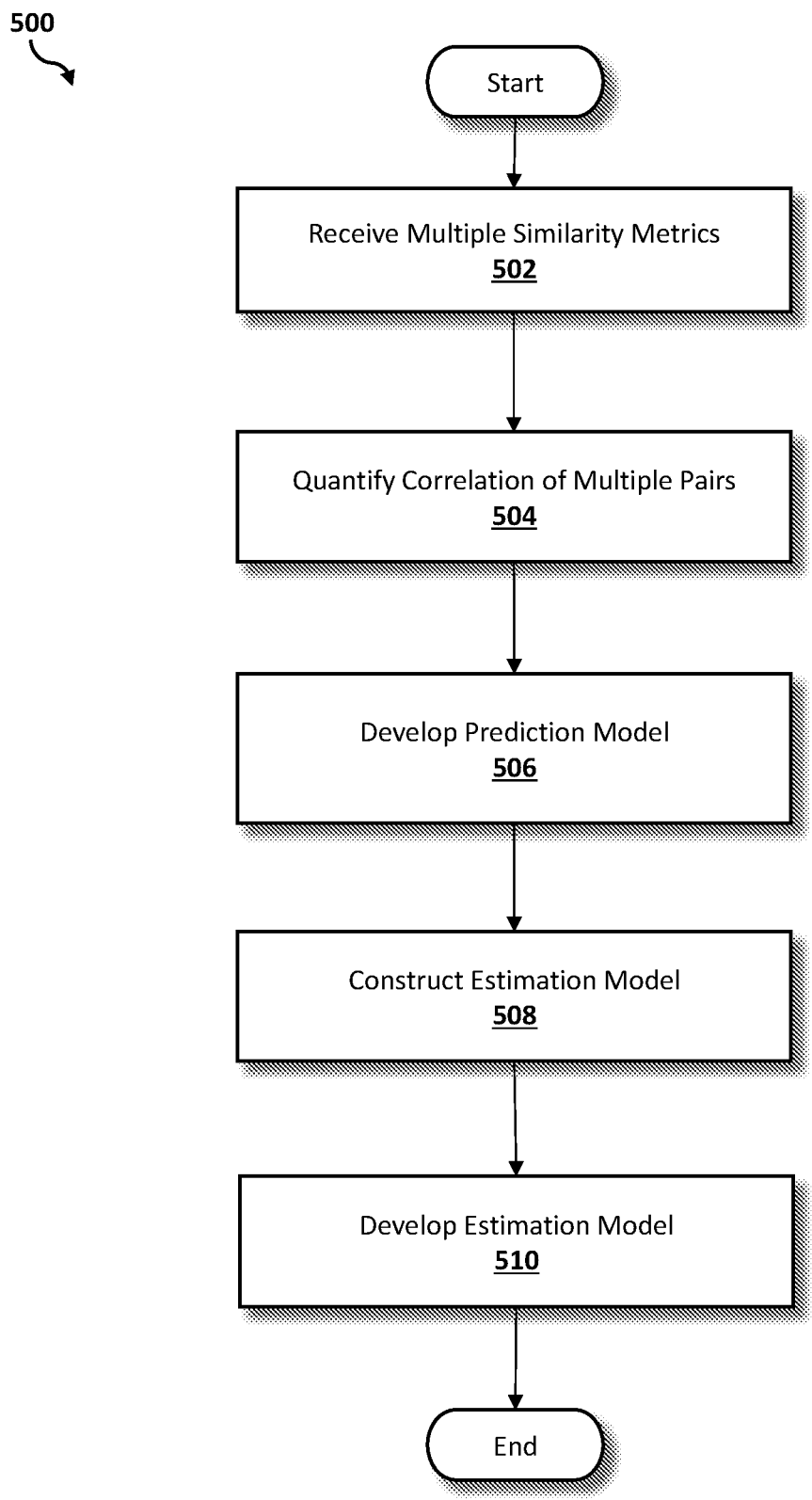
FIG. 5 is an operational flowchart illustrating a process for estimating error in at least one prediction associated with a data model according to at least one embodiment.

Referring now to FIG. 5, an operational flowchart illustrating the exemplary error estimation process 500 by used by the combined disease similarity metrics program 110a, 110b according to at least one embodiment is depicted.

As shown, multiple similarity metrics are received at 502 (i.e., receive multiple similarity metrics 302), and then, at 504, a correlation of multiple pairs is quantified (i.e., quantify correlation of multiple pairs 304). Then, at 506, the combined disease similarity metrics program 110a, 110b may develop a predictive model m1 to calculate disease-gene associations for a set of disease, gene pairs S, whose values for c1 are known, to estimate the accuracy of a predictive model m1 for disease-gene associations. Additionally, the combined disease similarity metrics program 110a, 110b may then utilize the predictive model m1 to determine a set of error values E comprised of the differences between the actual values for pairs in S and the predicated (or estimated) values for pairs in S. Then, at 508, the combined disease similarity metrics program 110a, 110b may construct an accuracy determination model m2 (i.e., estimation model or trained model) on the training set E to predict the accuracy of predictions generated on the predictive model m1.

Then, at 510, the estimation model m2 is developed to estimate the error in the predictive model m1, by utilizing at least one of the following input parameters:

(1) number of entities (i.e., predictive diseases and genes) used to predict a value of c1 (i.e., G1 values);

(2) a sum of s1 values for entities used to predict a value of c1 (i.e., G1 values);

(3) number of similarity metrics (i.e., predictive pairs) used to predict a value of c1 (i.e., G1 values);

(4) a variance or standard of deviation in known values of c1 (i.e., G1 values) used to predict a value of c1 (i.e., using Formula 1 and/or Formula 2); and (5) the weighted variance or standard deviation in known values of c1 (i.e., G1 values) used to predict a value of c1 (i.e., using Formula 1 and/or Formula 2).

In the present embodiment, the combined disease similarity metrics program 110a, 110b may optionally tune m2 using other data, thereby the combined disease similarity metrics program 110a, 110b may use m2 to predict error values for predictive model m1.

Users are often interested in the accuracy of predictions. The methods, systems and/or computer program products used by the combined disease similarity metrics program 110a, 110b described above may estimate error in predictions, such as disease-gene association predictions and predictions about effective treatments for diseases, and may be utilized to quantify error in predictions.

In another embodiment, the output generated by the combined disease similarity metrics program 110a, 110b (e.g., multiple similarity metrics, quantified correlation of multiple pairs, prediction models, and estimation models) may be stored in a database (e.g., database 114) for future access and may be used to improve the function of the combined disease similarity metrics program 110a, 110b operated by the user device (e.g., user's computer 102). For example, the combined disease similarity metrics program 110a, 110b may utilize the stored output or data in the database when constructing, developing and training a prediction model and estimation model (i.e., data models). The database may be indexed, for example, by the type of genes and diseases that are associated with the output. Additionally, the user may be able to configure the database associated with the combined disease similarity metrics program 110a, 110b to index based on different variables.

It may be appreciated that FIGS. 2-5 provide only an illustration of one embodiment and do not imply any limitations with regard to how different embodiments may be implemented. Many modifications to the depicted embodiment(s) may be made based on design and implementation requirements.

Figure 6:
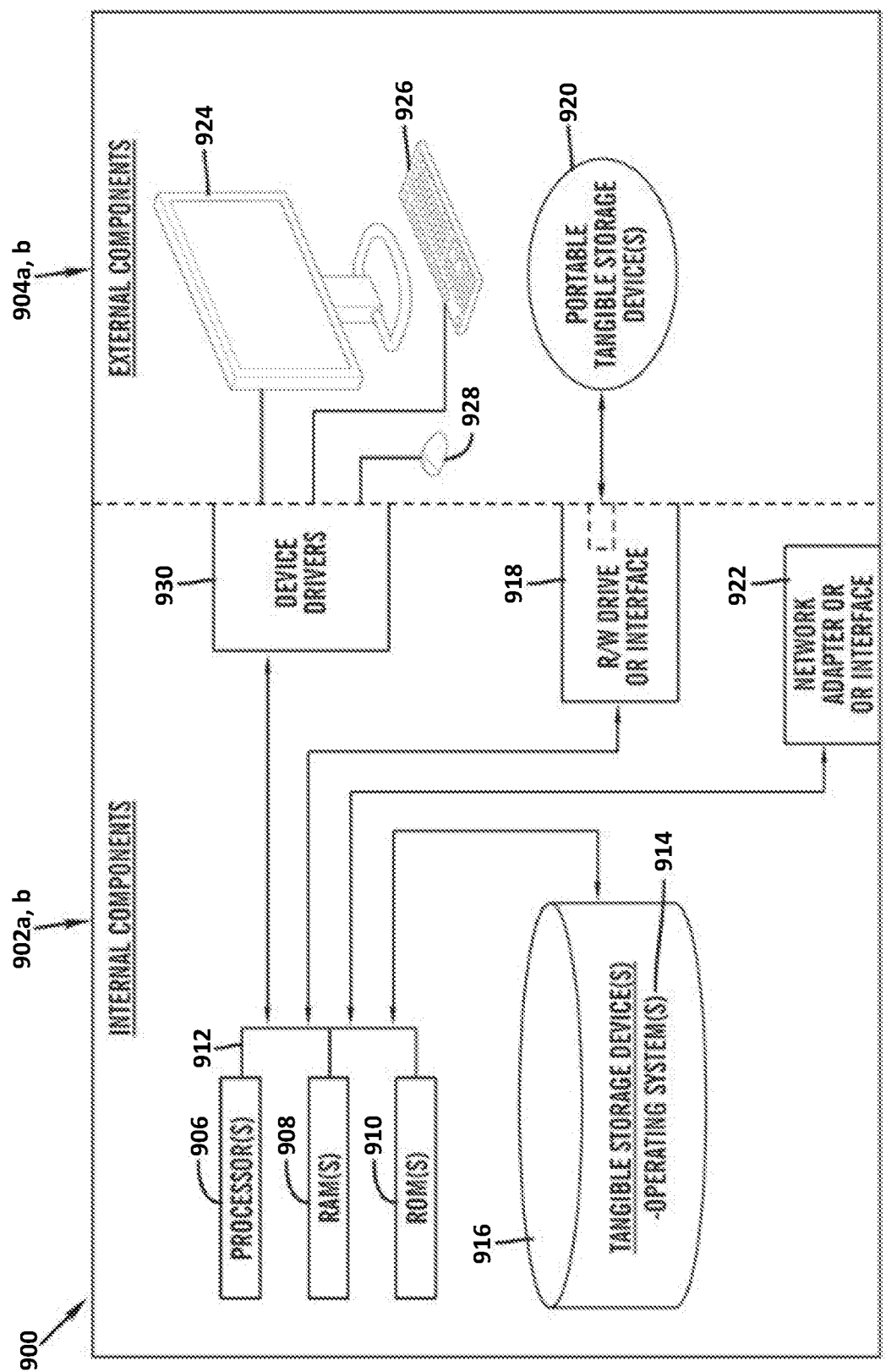
FIG. 6 is a block diagram of internal and external components of computers and servers depicted in FIG. 1 according to at least one embodiment.

FIG. 6 is a block diagram 900 of internal and external components of computers depicted in FIG. 1 in accordance with an illustrative embodiment of the present invention. It should be appreciated that FIG. 6 provides only an illustration of one implementation and does not imply any limitations with regard to the environments in which different embodiments may be implemented. Many modifications to the depicted environments may be made based on design and implementation requirements.

Data processing system 902, 904 is representative of any electronic device capable of executing machine-readable program instructions. Data processing system 902, 904 may be representative of a smart phone, a computer system, PDA, or other electronic devices. Examples of computing systems, environments, and/or configurations that may be represented by data processing system 902, 904 include, but are not limited to, personal computer systems, server computer systems, thin clients, thick clients, hand-held or laptop devices, multiprocessor systems, microprocessor-based systems, network PCs, minicomputer systems, and distributed cloud computing environments that include any of the above systems or devices.

User client computer 102 and network server 112 may include respective sets of internal components 902 *a, b* and external components 904 *a, b* illustrated in FIG. 6. Each of the sets of internal components 902 *a, b* includes one or more processors 906, one or more computer-readable RAMs 908 and one or more computer-readable ROMs 910 on one or more buses 912, and one or more operating systems 914 and one or more computer-readable tangible storage devices 916. The one or more operating systems 914, the software program 108 and the combined disease similarity metrics program 110a in client computer 102, and the combined disease similarity metrics program 110b in network server 112, may be stored on one or more computer-readable tangible storage devices 916 for execution by one or more processors 906 via one or more RAMs 908 (which typically include cache memory). In the embodiment illustrated in FIG. 6, each of the computer-readable tangible storage devices 916 is a magnetic disk storage device of an internal hard drive. Alternatively, each of the computer-readable tangible storage devices 916 is a semiconductor storage device such as ROM 910, EPROM, flash memory or any other computer-readable tangible storage device that can store a computer program and digital information.

Each set of internal components 902 *a, b* also includes a R/W drive or interface 918 to read from and write to one or more portable computer-readable tangible storage devices 920 such as a CD-ROM, DVD, memory stick, magnetic tape, magnetic disk, optical disk or semiconductor storage device. A software program, such as the software program 108 and the combined disease similarity metrics program 110a, 110b can be stored on one or more of the respective portable computer-readable tangible storage devices 920, read via the respective R/W drive or interface 918 and loaded into the respective hard drive 916.

Each set of internal components 902 *a, b* may also include network adapters (or switch port cards) or interfaces 922 such as a TCP/IP adapter cards, wireless Wi-Fi interface cards, or 3G or 4G wireless interface cards or other wired or wireless communication links. The software program 108 and the combined disease similarity metrics program 110a in client computer 102 and the combined disease similarity metrics program 110b in network server computer 112 can be downloaded from an external computer (e.g., server) via a network (for example, the Internet, a local area network or other, wide area network) and respective network adapters or interfaces 922. From the network adapters (or switch port adaptors) or interfaces 922, the software program 108 and the combined disease similarity metrics program 110a in client computer 102 and the combined disease similarity metrics program 110b in network server computer 112 are loaded into the respective hard drive 916. The network may comprise copper wires, optical fibers, wireless transmission, routers, firewalls, switches, gateway computers and/or edge servers.

Each of the sets of external components 904 *a, b* can include a computer display monitor 924, a keyboard 926, and a computer mouse 928. External components 904 *a, b* can also include touch screens, virtual keyboards, touch pads, pointing devices, and other human interface devices. Each of the sets of internal components 902 *a, b* also includes device drivers 930 to interface to computer display monitor 924, keyboard 926 and computer mouse 928. The device drivers 930, R/W drive or interface 918 and network adapter or interface 922 comprise hardware and software (stored in storage device 916 and/or ROM 910).

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Analytics as a Service (AaaS): the capability provided to the consumer is to use web-based or cloud-based networks (i.e., infrastructure) to access an analytics platform. Analytics platforms may include access to analytics software resources or may include access to relevant databases, corpora, servers, operating systems or storage. The consumer does not manage or control the underlying web-based or cloud-based infrastructure including databases, corpora, servers, operating systems or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 7:
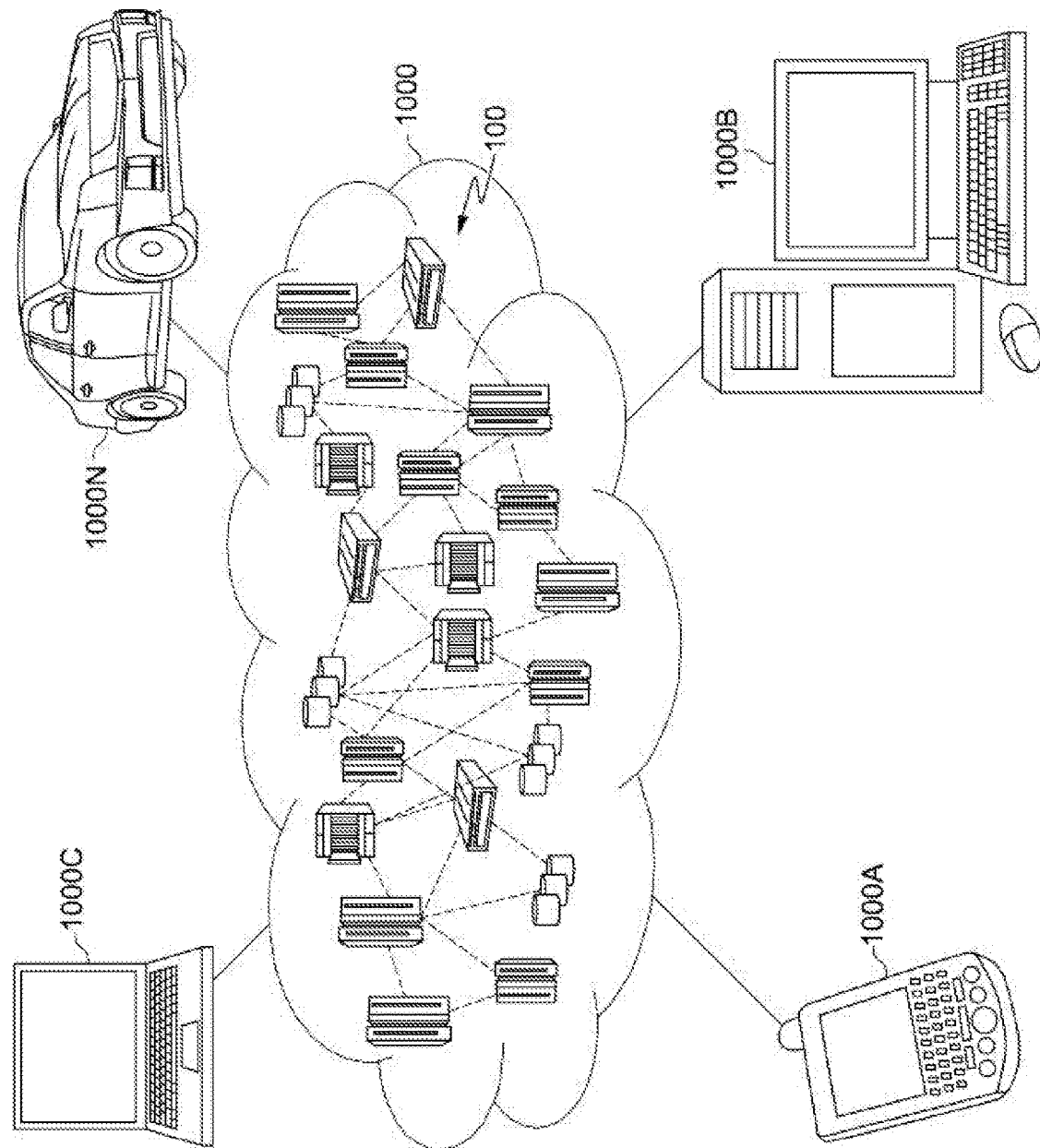
FIG. 7 is a block diagram of an illustrative cloud computing environment including the computer system depicted in FIG. 1, in accordance with an embodiment of the present disclosure.

Referring now to FIG. 7, illustrative cloud computing environment 1000 is depicted. As shown, cloud computing environment 1000 comprises one or more cloud computing nodes 100 with which local computing devices used by cloud consumers, such as, for example, personal digital assistant (PDA) or cellular telephone 1000A, desktop computer 1000B, laptop computer 1000C, and/or automobile computer system 1000N may communicate. Nodes 100 may communicate with one another. They may be grouped (not shown) physically or virtually, in one or more networks, such as Private, Community, Public, or Hybrid clouds as described hereinabove, or a combination thereof. This allows cloud computing environment 1000 to offer infrastructure, platforms and/or software as services for which a cloud consumer does not need to maintain resources on a local computing device. It is understood that the types of computing devices 1000A-N shown in FIG. 7 are intended to be illustrative only and that computing nodes 100 and cloud computing environment 1000 can communicate with any type of computerized device over any type of network and/or network addressable connection (e.g., using a web browser).

Figure 8:
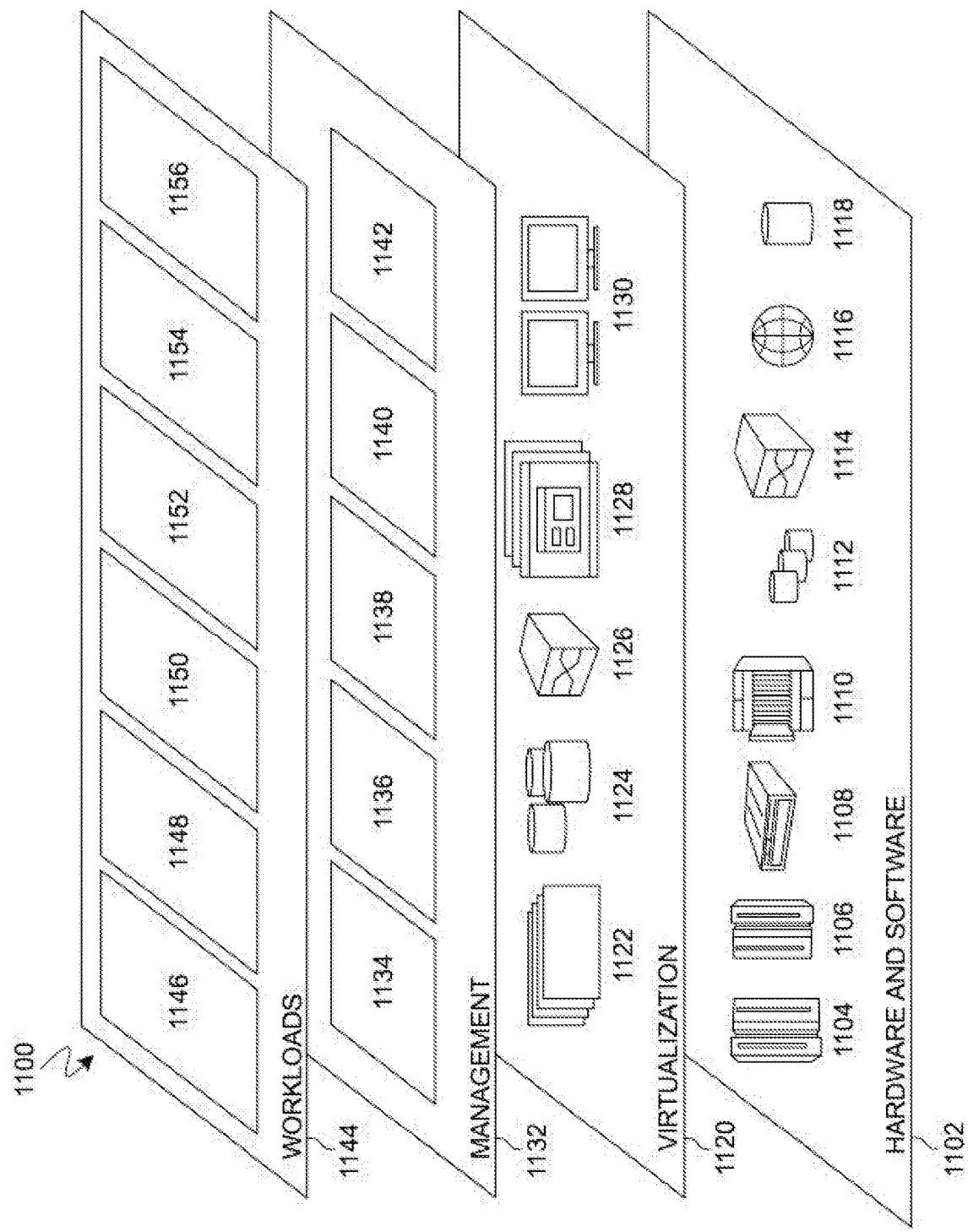
FIG. 8 is a block diagram of functional layers of the illustrative cloud computing environment of FIG. 7, in accordance with an embodiment of the present disclosure.

Referring now to FIG. 8, a set of functional abstraction layers 1100 provided by cloud computing environment 1000 is shown. It should be understood in advance that the components, layers, and functions shown in FIG. 8 are intended to be illustrative only and embodiments of the invention are not limited thereto. As depicted, the following layers and corresponding functions are provided:

Hardware and software layer 1102 includes hardware and software components. Examples of hardware components include: mainframes 1104; RISC (Reduced Instruction Set Computer) architecture based servers 1106; servers 1108; blade servers 1110; storage devices 1112; and networks and networking components 1114. In some embodiments, software components include network application server software 1116 and database software 1118.

Virtualization layer 1120 provides an abstraction layer from which the following examples of virtual entities may be provided: virtual servers 1122; virtual storage 1124; virtual networks 1126, including virtual private networks; virtual applications and operating systems 1128; and virtual clients 1130.

In one example, management layer 1132 may provide the functions described below. Resource provisioning 1134 provides dynamic procurement of computing resources and other resources that are utilized to perform tasks within the cloud computing environment. Metering and Pricing 1136 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 1138 provides access to the cloud computing environment for consumers and system administrators. Service level management 1140 provides cloud computing resource allocation and management such that required service levels are met. Service Level Agreement (SLA) planning and fulfillment 1142 provide pre-arrangement for, and procurement of, cloud computing resources for which a future requirement is anticipated in accordance with an SLA.

Workloads layer 1144 provides examples of functionality for which the cloud computing environment may be utilized. Examples of workloads and functions which may be provided from this layer include: mapping and navigation 1146; software development and lifecycle management 1148; virtual classroom education delivery 1150; data analytics processing 1152; transaction processing 1154; and combined disease similarity metrics 1156. A combined disease similarity metrics program 110a, 110b provides a way to use combined disease similarity metrics to make predictions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method for determining a composite similarity metric for data of a first data type comprising the steps of:
   providing a plurality of similarity metrics for the first data type;
   providing a metric quantifying correlation of entities belonging to the first data type and entities belonging to a second data type;
   developing a first regression model to predict values of the provided metric quantifying correlation of entities belonging to the first data type and entities belonging to the second data type using the provided plurality of similarity metrics;
   calculating the composite similarity metric from a plurality of first regression coefficients in the developed first regression model;
   providing a plurality of ground truth data sets; and
   developing at least one second regression model to predict values of the provided metric quantifying correlation of entities belonging to the first data type and entities belonging to the second data type using the plurality of similarity metrics for each ground truth data set.

2. The method of claim 1 in which the step of calculating the composite similarity metric, further comprises:
   calculating a sum of ai*di for each similarity metric di of the provided plurality of similarity metrics where ai is a regression coefficient from the plurality of first regression coefficients corresponding to di.

3. The method of claim 1, further comprising:
   calculating the composite similarity metric by adding a plurality of second regression coefficients corresponding to regression models for different ground truth data sets.

4. The method of claim 1, further comprising:
   calculating the composite similarity metric by adding a plurality of second regression coefficients corresponding to the developed at least one second regression model for different ground truth data sets weighted by an importance of a ground truth data set.

5. The method of claim 1 in which the first data type comprises diseases.

6. The method of claim 1 in which the second data type comprises genes.

7. The method of claim 1, further comprising:
   inferring a value of the provided metric quantifying correlation of a first entity belonging to the first data type and a second entity belonging to the second data type by determining a set of entities of the first data type for which a value of the metric quantifying correlation of an entity in the set of entities with the second entity is known and a value of a metric quantifying similarity between the first entity and an entity in the set of entities equals or exceeds a threshold.

8. The method of claim 7, further comprising:
   running a predictive algorithm to infer at least one known value of the metric quantifying correlation of entities belonging to the first data type and entities belonging to the second data type multiple times using different values for the threshold;
   determining a prediction accuracy associated with different values for the threshold; and
   selecting a value of the threshold to maximize the prediction accuracy.

9. The method of claim 1 in which the first regression model and second regression model are linear models.

10. A computer system for determining a composite similarity metric for data of a first data type, comprising:

one or more processors, one or more computer-readable memories, one or more computer-readable tangible storage medium, and program instructions stored on at least one of the one or more tangible storage medium for execution by at least one of the one or more processors via at least one of the one or more memories, wherein the computer system is capable of performing a method comprising:

providing a plurality of similarity metrics for the first data type;

providing a metric quantifying correlation of entities belonging to the first data type and entities belonging to a second data type;

developing a first regression model to predict values of the provided metric quantifying correlation of entities belonging to the first data type and entities belonging to the second data type using the provided plurality of similarity metrics;

calculating the composite similarity metric from a plurality of first regression coefficients in the developed first regression model;

providing a plurality of ground truth data sets; and developing at least one second regression model to predict values of the provided metric quantifying correlation of entities belonging to the first data type and entities belonging to the second data type using the plurality of similarity metrics for each ground truth data set.

11. The computer system of claim 10 in which the step of calculating the composite similarity metric, further comprises:
calculating a sum of ai*di for each similarity metric di of the provided plurality of similarity metrics where ai is a regression coefficient from the plurality of first regression coefficients corresponding to di.

12. The computer system of claim 10, further comprising:
calculating the composite similarity metric by adding a plurality of second regression coefficients corresponding to regression models for different ground truth data sets.

13. The computer system of claim 10, further comprising:
calculating the composite similarity metric by adding a plurality of second regression coefficients corresponding to the developed at least one second regression model for different ground truth data sets weighted by an importance of a ground truth data set.

14. The computer system of claim 10 in which the first data type comprises diseases.

15. The computer system of claim 10 in which the second data type comprises genes.

16. The computer system of claim 10, further comprising:
inferring a value of the provided metric quantifying correlation of a first entity belonging to the first data type and a second entity belonging to the second data type by determining a set of entities of the first data type for which a value of the metric quantifying correlation of an entity in the set of entities with the second entity is known and a value of a metric quantifying similarity between the first entity and an entity in the set of entities equals or exceeds a threshold.

17. The computer system of claim 16, further comprising:
running a predictive algorithm to infer at least one known value of the metric quantifying correlation of entities belonging to the first data type and entities belonging to the second data type multiple times using different values for the threshold;

determining a prediction accuracy associated with different values for the threshold; and selecting a value of the threshold to maximize the prediction accuracy.

18. The computer system of claim 10 in which the first regression model and second regression model are linear models.

19. A computer program product for determining a composite similarity metric for data of a first data type, comprising:

one or more processors, one or more computer-readable memories, one or more computer-readable tangible storage medium, and program instructions stored on at least one of the one or more tangible storage medium for execution by at least one of the one or more processors via at least one of the one or more memories, wherein the computer system is capable of performing a method comprising:

providing a plurality of similarity metrics for the first data type;

providing a metric quantifying correlation of entities belonging to the first data type and entities belonging to a second data type;

developing a first regression model to predict values of the provided metric quantifying correlation of entities belonging to the first data type and entities belonging to the second data type using the provided plurality of similarity metrics;

calculating the composite similarity metric from a plurality of first regression coefficients in the developed first regression model;

providing a plurality of ground truth data sets; and developing at least one second regression model to predict values of the provided metric quantifying correlation of entities belonging to the first data type and entities belonging to the second data type using the plurality of similarity metrics for each ground truth data set.

20. The computer program product of claim 19 in which the step of calculating the composite similarity metric, further comprises:
calculating a sum of ai*di for each similarity metric di of the provided plurality of similarity metrics where ai is a regression coefficient from the plurality of first regression coefficients corresponding to di.

21. The computer program product of claim 19, further comprising:
calculating the composite similarity metric by adding a plurality of second regression coefficients corresponding to regression models for different ground truth data sets.

22. The computer program product of claim 19, further comprising:
calculating the composite similarity metric by adding a plurality of second regression coefficients corresponding to the developed at least one second regression model for different ground truth data sets weighted by an importance of a ground truth data set.

* * * * *